United States Patent [19]

Carter et al.

[11] Patent Number: 5,489,599
[45] Date of Patent: Feb. 6, 1996

[54] PIPERIDINE DERIVATIVES

[75] Inventors: Paul A. Carter, Ingelheim, Germany; Steven J. Tapp, Faversham; Nicholas J. Daniels, Sittingbourne, both of England

[73] Assignee: Shell Research Limited, United Kingdom

[21] Appl. No.: 81,298

[22] PCT Filed: Jan. 8, 1992

[86] PCT No.: PCT/EP92/00040

§ 371 Date: Jun. 28, 1993

§ 102(e) Date: Jun. 28, 1993

[87] PCT Pub. No.: WO92/12130

PCT Pub. Date: Jul. 23, 1992

[30] Foreign Application Priority Data

Jan. 10, 1991 [GB] United Kingdom ............... 9100505

[51] Int. Cl.$^6$ .............. A01N 43/40; C07D 211/68; C07D 211/26; C07D 211/18

[52] U.S. Cl. .............. 514/317; 514/318; 514/319; 514/326; 514/331; 546/192; 546/193; 546/194; 546/705; 546/206; 546/209; 546/229; 546/250; 546/232; 546/236; 546/237; 546/238; 546/239; 546/240

[58] Field of Search ............... 546/192, 193, 546/194, 208, 206, 209, 229, 230, 232, 236, 237, 238, 239, 240; 514/317, 318, 319, 326, 331

[56] References Cited

U.S. PATENT DOCUMENTS 2,956,058  10/1960  Shepard et al. ............... 546/210
3,458,521  7/1969   Jack et al. ............... 546/210
4,656,282  4/1987   Himmele et al. ............... 546/184
4,785,006  11/1988  Worthington et al. ............... 514/314
5,051,409  9/1991   Zipplies et al. ............... 546/205
5,095,021  3/1992   Zipplies et al. ............... 514/317

FOREIGN PATENT DOCUMENTS 000333   1/1979   European Pat. Off. .
244739   11/1987  European Pat. Off. .
359400   3/1990   European Pat. Off. .
372776   6/1990   European Pat. Off. .
379085   7/1990   European Pat. Off. .
1421208  3/1966   France .
2096916  3/1972   France .
801792   9/1958   United Kingdom .
1044309  9/1966   United Kingdom .
2083476  3/1982   United Kingdom .
2177085  1/1987   United Kingdom .

Primary Examiner—C. Warren Ivy
Assistant Examiner—Raymond Covington

[57] ABSTRACT

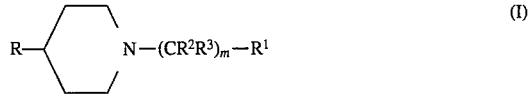

The invention provides piperidine derivatives of general formula (I) or an acid-addition salt thereof, in which R represents an optionally substituted alkyl, cycloalkyl, aryl or heterocyclyl group: $R^1$ represents an optionally substituted alkyl, alkenyl, akynyl, cycloalkyl, aryl or heterocyclyl group; m represents an integer from 0 to 3; and each of $R^2$ and $R^3$ is independently selected from a group consisting of hydrogen atoms, alkyl and phenyl groups; with the proviso that R does not represent a 4-tert-butylphenyl group; processes for their preparation; compositions containing such compounds and their use as fungicides.

25 Claims, No Drawings

PIPERIDINE DERIVATIVES

This invention relates to certain piperidine derivatives, a process for their preparation, compositions containing such compounds and their use as fungicides.

DE-A-3614907 discloses compounds of the general formula

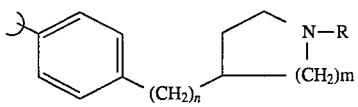

in which R represents a $C_{1-20}$ alkyl, $C_{2-20}$ alkoxyalkyl, $C_{2-20}$ hydroxyalkyl, $C_{3-12}$ cycloalkyl, $C_{4-20}$ alkylcycloalkyl, $C_{4-20}$ cycloalkylalkyl, aryl, haloaryl, $C_{7-20}$ aralkyl, $C_{7-20}$ haloaralkyl or $C_{7-20}$ aryloxyalkyl group, m is 1 or 2 and n is 0 or 1, some of which are said to exhibit better activity than Fenpropimorph against certain phytopathogenic fungi. Compounds in which m is 2, that is, piperidine derivatives substituted at the 1- and 4- positions, and n is 0 are said to be especially preferred.

It has now been discovered that certain other piperidine derivatives substituted at the 1- and 4-positions, but not at the 4-position by a substituent containing a 4-tert-butylphenyl group, are highly active against certain phytopathogenic fungi. According to the present invention there is therefore provided a compound of the general formula

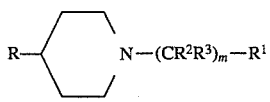

or an acid addition salt thereof, in which R represents an optionally substituted alkyl, cycloalkyl, aryl or heterocyclyl group; $R^1$ represents an optionally substituted alkyl, alkenyl, alkynyl, cycloalkyl, aryl or heterocyclyl group; m represents an integer from 0 to 3; and each of $R^2$ and $R^3$ is independently selected from a group consisting of hydrogen atoms, alkyl and phenyl groups; with the proviso that R does not represent a 4-tert-butylphenyl group.

When the compounds of this invention contain an alkyl, alkenyl or alkynyl substituent group, this may be linear or branched and may contain up to 12, preferably up to 8, and especially up to 6, carbon atoms. A cycloalkyl group may contain from 3 to 5, preferably 3 to 6, carbon atoms. An aryl group may be any aromatic hydrocarbon group, especially a phenyl or naphthyl group. A heterocyclyl group may be any saturated or unsaturated ring system containing at least one heteroatom, 5- and 6- membered rings being especially preferred.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, halophenyl and phenoxy groups. When any of the foregoing substituents represents or contains an alkyl substituent group, this may be linear or branched and may contain up to 12, preferably up to 6, and especially up to 4, carbon atoms.

It is preferred that R represents a naphthyl group or a phenyl group optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkyl amino, di-$C_{1-4}$ alkylamino, formyl, $C_{1-4}$ alkoxycarbonyl carboxyl and phenyl groups.

More preferably, R represents a naphthyl group or a phenyl group optionally substituted by a halogen, especially a fluorine chlorine or bromine, atom or a nitro, $C_{1-4}$ alkyl, $C_{1-4}$ alkoxy, amino or phenyl group.

It is preferred that $R^1$ represents a $C_{1-12}$ alkyl, $C_{2-12}$ alkenyl, $C_{2-12}$ alkynyl, $C_{3-8}$ cycloalkyl, naphthyl, phenyl, pyridyl or thiazolyl group, each group being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, halophenyl and phenoxy groups.

More preferably, $R^1$ represents a $C_{1-8}$ alkyl, $C_{2-8}$ alkenyl, $C_{2-8}$ alkynyl, $C_{3-6}$ cycloalkyl, naphthyl, phenyl, pyridyl or thiazolyl group, each group being optionally substituted by one or more substituents selected from halogen, especially fluorine, chlorine and bromine atoms, nitro, cyano, $C_{1-4}$ alkyl, $C_{1-4}$ haloalkyl, $C_{1-4}$ alkoxy, $C_{1-4}$ alkoxycarbonyl, phenyl, halophenyl and phenoxy groups.

It is also preferred that each of $R^2$ and $R^3$ is independently selected from a group consisting of hydrogen atoms, $C_{1-4}$ alkyl, especially methyl, and phenyl groups.

A particularly preferred sub-group of compounds of formula I is that in which R represents a naphthyl, phenyl, fluorophenyl, chlorophenyl, bromophenyl, nitrophenyl, methylphenyl, methoxyphenyl, aminophenyl or biphenyl group, $R^1$ represents an ethyl, propyl, butyl, pentyl, hexyl, heptyl, octyl, phenoxyethyl, propenyl, butenyl, pentenyl, hexenyl, phenylpropenyl, propynyl, butynyl, pentynyl, hexynyl, cyclohexyl, hydroxycyclohexyl, naphthyl, phenyl, fluorophenyl, chlorophenyl, dichlorophenyl, bromophenyl, nitrophenyl, cyclophenyl, methylphenyl, butylphenyl, trifluoromethylphenyl, methoxyphenyl, methoxycarbonylphenyl, biphenylyl, pyridyl or chlorphenyl-thiazolyl group; $R^2$ represents a hydrogen atom or a methyl or phenyl group and $R^3$ represents a hydrogen atom.

The compounds of formula I may form acid addition salts with a variety of acids. However, acid addition salts with acids such as saccharin, aliphatic and aromatic carboxylic acids, such as acetic, lauric, benzoic, oxalic, lactic and mandelic acids, aliphatic and aromatic sulphonic acids, such as dodecylbenzenesulphonic acid, and mineral acids, particularly phosphonic and hydrochloric acid, are especially preferred.

It should also be appreciated that some of the compounds of formula I are capable of existing as different geometric isomers and diastereomers. The invention thus includes both the individual isomers and mixtures of such isomers.

The present invention also provides a process for the preparation of a compound of formula I as defined above or an acid-addition salt thereof which comprises reacting a compound of the general formula

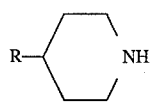

in which R is as defined above, or an acid addition salt thereof, with a compound of the general formula

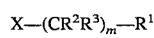

in which m, $R^1$ $R^2$ and $R^3$ are as defined above and X represents a leaving group, and, if desired, reacting the compound of formula I so obtained with a suitable acid to form an acid addition salt thereof.

Preferably, the leaving group is a halogen, especially a bromine, atom or a sulphonate group, such as a methylsulphonate or toluenesulphonate group.

The process of the invention is conveniently carried out in the presence of a solvent. Suitable solvents include ethers, particularly tetrahydrofuran, and dimethylformamide. The reaction is suitably carried out at temperature of 0° to 160° C., the preferred reaction temperature being 20° to 120° C. It is also preferred that the reaction is carried out in the presence of a base, such as potassium carbonate.

Compounds of formula II in which R represents a heterocyclyl group, a naphthyl group or a phenyl group optionally substituted by a chlorine atom or a $C_{1-4}$ alkyl group may be conveniently prepared by reacting a compound of the general formula

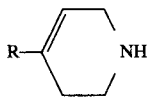
(IV)

with a hydrogenating agent, such as hydrogen with a palladium on charcoal catalyst.

Compounds of formula II other than those referred to in the preceding paragraph and those in which R represents a nitrophenyl group may be conveniently prepared from compounds of formula II in which R represents an aminophenyl group via a Sandmeyer reaction. For instance, a compound of formula II in which R represents an aminophenyl group may be reacted with sodium nitrite in the presence of a mineral acid, such as hydrochloric, hydrobromic or tetrafluoroboric acid, in aqueous solution to form a diazonium salt which is then reacted with an appropriate copper (I) salt, such as copper (I) fluoride, copper (I) bromide, copper (I) cyanide etc, to form a compound of formula II in which R represents a fluorophenyl, bromophenyl, cyanophenyl etc group. Other compounds of formula II may then be formed by manipulation of the cyanophenyl group in the compound of formula II where R represents a cyanophenyl group using processes analogous to known processes.

Compounds of formula II in which R represents an aminophenyl group may be prepared by reacting a compound of formula II in which R represents a nitrophenyl group with a suitable reducing agent, such as hydrogen with a palladium on charcoal catalyst.

Compounds of formula II in which R represents a nitrophenyl group may be prepared by reacting a compound of formula II in which R represents a phenyl group with a mixture of concentrated nitric acid and concentrated sulphuric acid.

Compounds of formula II in which R represents a phenyl group are known compounds or may be prepared by hydrogenation of a compound of formula IV, as described above, Compounds of formula IV can be prepared by the method described in JP-90 53793 (Sumitomo).

Alternatively, compounds of formula II may be conveniently prepared by reacting a compound of the general formula

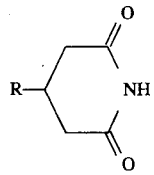
(V)

in which R is as hereinbefore defined, with a suitable reducing agent, such as lithium aluminium hydride.

Compounds of formula V may be prepared by treating the corresponding glutaric acid with acetic anhydride and concentrated ammonium hydroxide according to the method of L. M. Rice, M. E. Freed, C. H. Grogan, J. Org. Chem., 29, (1964), 2637.

The appropriate glutaric acid may be prepared by treating the corresponding cyclohexanone with a base, such as sodium hydroxide, and the appropriate cyclohexanone may be prepared by reacting a compound of the general formula

(VI)

in which R is as hereinbefore defined, with ethylacetoacetate and piperidine according to the method of W. T. Smith and P. G. Kort, J. Amer. Chem. Soc., 72, (1950), 1877. (NB. The structural assignment of the product in the latter reference is incorrect as the cyclohexanone described above is, in fact, formed by this method and not the ethyl benzal-bis-acetoacetates as stated therein).

Compounds of formula III and VI are known compounds or can be prepared by processes analogous to known processes.

The compounds of general formula I have been found to have fungicidal activity. Accordingly, the invention further provides a fungicidal composition which comprises a carrier and, as active ingredient, a compound of formula I or an acid-addition salt or metal salt complex thereof as defined above. A method of making such a composition is also provided which comprises bringing a compound of formula I as defined above, or an acid-addition salt or metal salt complex thereof, into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and stytens polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide, fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate, and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ⅓–10% w of active ingredient. Granules are usually prepared to have a size between 10 and 100 BS mesh (1.676–0.152 mm), and may be manufactured by agglomeration or impregnation techniques. Generally, granules will contain ⅓–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or an acid-addition salt or metal salt complex thereof or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include vines, grain crops such as wheat and barley, rice, broad beans and tomatoes. The duration of protection is normally dependent on the individual compound selected, and also a variety of external factors, such as climate, whose impact is normally mitigated by the use of a suitable formulation.

Certain compounds of formula II also exhibit fungicidal activity. For instance, the compounds of formula II in which R represents a phenyl or 4-bromophenyl group show good activity against *Plasmopara viticola* in vines.

The invention is further illustrated by the following examples.

EXAMPLE 1

Preparation of N-benzyl-4-(4-chlorophenyl) piperidine. (R-4-chlorophenyl; $R^1$=phenyl; m=1; $R^2$=$R^3$=hydrogen)

(i) Preparation of 4-(4-chlorophenyl) piperidine

A solution of 4-(4-chlorophenyl)-1,2,5,6-tetrahydropyridine (10.0 g, 52 mmol) in ethyl acetate (200 ml) containing 5% palladium on charcoal was hydrogenated at approximately 3 atmospheres until uptake of hydrogen ceased. The reaction was then filtered through "Hyflo" (Trade Mark:diatomaceous earth) and evaporated in vacuo to give the desired product as an off-white solid (10.0 g, 99% yield), m.pt. 143° C. Low resolution mass spectroscopy revealed the mass/charge ratio of the parent molecule ion, $M^+$, to be 195/197.

Analysis: Calc. C:67.5; H:7.2; N:7.2%. Found C:66.5; H:8.2; N:6.9%.

(ii) Preparation of N-benzyl-4-(4-chlorophenyl) piperidine

A mixture of the 4-(4-chlorophenyl) piperidine (2.0 g, 10.2 mmol) obtained in (i), benzyl bromide (1.22 ml, 10.2 mmol) and potassium carbonate (4.26 g, 30.6 mmol) in tetrahydrofuran (100 ml) was heated under reflux for 2 days. The reaction mixture was then cooled, evaporated in vacuo and ethyl acetate (100 ml) added. This was then washed with brine (2×100 ml) and the organic phase dried with magnesium sulphate. Evaporation of the solvent followed by flash column chromatography on silica gel using ethyl acetate as eluant gave 2.21 g (76% yield) N-benzyl-4-(4-chlorophenyl) piperidine as a yellow oil, $M^+$ found: 285/287.

Analysis: Calc. C:75.6; H:7.1; N:4.9%. Found C:82.9; H:8.0; N:5.2%.

EXAMPLE 2

Preparation of N-benzyl-4-(4-bromophenyl) piperidine (R=4-bromophenyl; $R^1$=phenyl, m=1; $R^2=R^3$=hydrogen)

(i) Preparation of 4-(4-nitrophenyl) piperidine

4-Phenylpiperidine (22 g, 0.14 mol) was dissolved in concentrated sulphuric acid (44 g) and concentrated nitric acid (12 ml) was then added dropwise such that the temperature did not rise above 5° C. The reaction was then warmed slowly to room temperature and stirred overnight. The reaction mixture was then poured into water and made basic with 2N aqueous potassium hydroxide. After extraction with ether (3×150 ml), the combined organic extracts were dried with sodium sulphate and evaporated in vacuo. Recrystallisation from diethyl ether afforded the desired product as yellow crystals (11.4 g, 40% yield), M.pt. 90°–92° C.

Analysis: Calc. C 64.1; H 6.8; N 13.6%. Found C 63.4; H 6.87 N 13.7%.

(ii) Preparation of 4-(4-aminophenyl) piperidine

A solution of the 4-(4-nitrophenyl) piperidine (29.3 g, 0.144 mol) obtained in (i) in ethyl acetate (150 ml) was hydrogenated at 3 atmospheres over Raney Nickel (5 g) until uptake of hydrogen ceased. Evaporation afforded a brown oil which was crystallised from ether to give the desired product as light yellow crystals (18.5 g, 74% yield), M.pt. 85°–87° C.

Analysis Calc. C 75.0; H 9.2; N 15.9%. Found C 73.3; H 8.9; N 15.6%.

(iii) Preparation of 4-(4-bromophenyl) piperidine 4-(4-Aminophenyl) piperidine (4.4 g, 25mmol) obtained in (ii) was dissolved in 50% (w/v) hydrobromic acid (8 ml) at 0° C. A solution of sodium nitrite (0.46 g) in water (5 ml) was added dropwise over a period of 10 minutes. After a further 30 minutes this mixture was poured slowly into a solution of copper (I) bromide (1.13 g, 7.9 mmol) in 50% hydrobromic acid (8 ml). The reaction mixture was allowed to warm slowly to room temperature with stirring and then heated at 40° C. for 1 hour. The reaction mixture was then cooled and poured into aqueous ammonia solution and extracted with chloroform (3×20 ml). The combined organic phases were dried with magnesium sulphate and evaporated to yield the desired product as a brown oil (4.0 g, 66% yield).

(iv) Preparation of N-benzyl-4-(4-bromophenyl) piperidine

The crude 4-(4-bromophenyl) piperidine (1.0 g, 4.2 mmol) obtained in (iii), benzyl bromide (0.72 g, 4.2 mmol) and potassium carbonate (0.75 g, 5.5 mmol) in tetrahydrofuran (50 ml) were heated under reflux with stirring for 4 hours. The reaction mixture was then cooled, poured into water and extracted with ethyl acetate (3×50 ml). The combined organic extracts were dried with sodium sulphate and evaporated. Column chromatography upon silica gel using 3:1 toluene:ethyl acetate as eluant gave N-benzyl-4-(4-bromophenyl) piperidine as a yellow oil (0.69 g, 53% yield).

Analysis Calc. C:65.5; H:6.1; N:4.2%. Found C:65.2; H:6.1; N:4.6%.

EXAMPLE 3

Preparation of N-benzyl-4-(4'-phenyl)phenylpiperidine (R=4-biphenylyl; $R^1$=phenyl; m=1; $R^2=R^3$=hydrogen)

(i) Preparation of 2,4-di(ethoxycarbonyl)-5-hydroxy-5-methyl-3-(4'-phenyl)phenylcyclohexanone A mixture of 4-phenylbenzaldehyde (40.0 g, 0.22 mol), ethylacetoacetate (57.3 g, 0.44 mol) and piperidine (4.4 g) in ethanol (10 ml) was allowed to stand for 24 hours. The resulting precipitate was then filtered off and recrystallised from ethanol to afford the product as white crystals (72.8 g), M.pt. 188°–190° C.

Analysis Calc. C:69.9; N:6.8%. Found C:70.2; N:6.6%.

(ii) Preparation of 3-(4'-phenyl)phenylglutaric acid

Treatment of the 2,4-di(ethoxycarbonyl)-5-hydroxy-5-methyl-3-(4'-phenyl)phenylcyclohexanone (70 g, 0.165 mol) obtained in (i) in ethanol (800 ml) with 50% (by weight) aqueous sodium hydroxide (970 g) at reflux for 4 hours was followed by pouring into water (500 ml). The ethanol was then distilled off and the residue acidified with conc. hydrochloric acid to approx. pH3. After standing at 5° C. for 3 hours the precipitate was filtered off and washed with water. Drying in vacuo afforded 35 g 3-(4'-phenyl)phenylglutaric acid as light brown crystals which were recrystallised from aqueous ethanol, M.pt.: 205°–207° C.

Analysis Calc. C:71.8; H:5.7%. Found C:71.8; H:5.6%.

(iii) Preparation of 4-(4'-phenyl)phenylpiperidin-2,6-dione

Treatment of the 3-(4'-phenyl)phenyl glutaric acid (30.0 g, 0.11 mol) obtained in (ii) with acetic anhydride (120 g) at reflux was followed by distillation of the remaining acetic anhydride. The resulting solid was then heated at reflux, for 2 hours with conc. aqueous ammonium hydroxide (30 ml). The excess ammonia was evaporated off and the residue partitioned between chloroform and saturated aqueous sodium bicarbonate. After drying over magnesium sulphate, the organic phase was evaporated in vacuo and the resulting solid triturated with ethyl acetate to afford 14 g 4-(4'-phenyl)phenylpiperidin- 2,6-dione as a tan solid. M.pt.: 115°–116° C.

Analysis Calc. C:77.0; H:5.7; N:5.3%. Found C:76.5; H:5.3; N:5.5%.

(iv) Preparation of 4-(4'-phenyl)phenylpiperidine

A solution of the 4-(4'-phenyl)phenylpiperidin- 2,6-dione (14.5 g, 0.055 mol) obtained in (iii) in tetrahydrofuran (100 ml) was added dropwise to a suspension of lithium aluminium hydride (6.2 g, 0.16 mol) in tetrahydrofuran (300 ml) with stirring. The reaction was then heated at reflux for 20 hours. After cooling, the reaction was worked up with saturated aqueous sodium sulphate and the precipitated solids filtered off through Tonsil (Trade mark, diatomaceous earth) which was washed well with ethyl acetate. Evaporation in vacuo followed by trituration with diisopropyl ether afforded 7.9 g 4-(4'-phenyl)phenylpiperidine as a white solid, M.pt. 106° C.

Analysis Calc. C:86.0; H:8.1; N:5.9%. Found C:84.1; H:8.1; N:5.8%.

(v) Preparation of N-benzyl-4-(4'-phenyl)phenylpiperidine

A mixture of the 4-(4'-phenyl)phenyl piperidine (1.2 g, 5 mmol) obtained in (iv), benzylbromide (0.86 g, 5 mmol), potassium carbonate (1.1 g, 8 mmol) and tetrahydrofuran (50 ml) were heated under reflux for 7 hours. After cooling, water was added and the reaction extracted with ethyl acetate (3 times). Drying over magnesium sulphate, evaporation in vacuo and flash column chromatography upon silica gel using 4:1 petroleum ether: ethylacetate as eluant afforded 0.9 g N-benzyl-4-(4'-phenyl)phenylpiperidine as a white solid M.pt.: 103° C.

Analysis Calc. C:88.0; H:7.7; N:4.3%. Found C:87.9; H:7.5; N:3.6%.

EXAMPLES 4 to 87

By processes similar to those described in Examples 1, 2 and 3 above, further compounds according to the invention were prepared as detailed in Table I below. In this table, the compounds are identified by reference to formula I.

TABLE I

| Ex No. | R | $R^1$ | m | $R^2$ | $R^3$ | C Calc. | C Found | H Calc. | H Found | N Calc. | N Found | M+ Found | Mpt. (°C.) |
|---|---|---|---|---|---|---|---|---|---|---|---|---|---|
| 4 | phenyl | 4-chlorophenyl | 1 | —H | —H | 75.6 | 75.3 | 7.1 | 7.2 | 4.9 | 5.0 | 261/263 | 66–67 |
| 5 | phenyl | phenyl | 1 | —H | —H | 86.0 | 88.0 | 8.4 | 8.7 | 5.6 | 5.6 | 227 | 35 |
| 6 | phenyl | phenyl | 2 | —H | —H | 86.0 | 86.0 | 8.7 | 8.8 | 5.3 | 5.8 | 241 | 66 |
| 7 | phenyl | n-$C_6H_{13}$ | 0 | — | — | 83.2 | 83.9 | 11.1 | 11.3 | 5.7 | 5.8 | 245 | |
| 8 | phenyl | 4-chlorophenyl | 2 | —H | —H | 76.1 | 73.5 | 7.4 | 6.8 | 4.7 | 4.3 | 299/301 | 73 |
| 9 | 4-chlorophenyl | n-$C_3H_7$ | 3 | —H | —H | 73.0 | 81.2 | 9.4 | 11.0 | 5.0 | 5.6 | 279/281 | |
| 10 | 4-chlorophenyl | phenyl | 2 | —H | —H | 76.1 | 84.0 | 7.4 | 8.9 | 4.7 | 5.2 | 299/301 | 48 |
| 11 | phenyl | n-$C_4H_9$ | 2 | —H | —H | 83.2 | 83.9 | 11.1 | 11.3 | 5.7 | 5.8 | 245 | |
| 12 | 4-chlorophenyl | n-$C_5H_{11}$ | 1 | —H | —H | 73.0 | 81.2 | 9.4 | 11.0 | 5.0 | 5.6 | 279/281 | |

| Example No. | R | $R^1$ | m | $R^2$ | $R^3$ | | Analysis C | H | N | Mpt. (°C.) |
|---|---|---|---|---|---|---|---|---|---|---|
| 13 | phenyl | 4-F phenyl | 1 | H | H | Calc. | 80.3 | 7.5 | 5.2 | 66–68 |
| | | | | | | Found | 80.0 | 7.6 | 5.2 | |
| 14 | " | 4-$NO_2$ phenyl | " | " | " | Calc. | 73.0 | 6.8 | 9.5 | 103–105 |
| | | | | | | Found | 72.5 | 6.8 | 9.4 | |
| 15 | " | 3-Cl phenyl | " | " | " | Calc. | 75.6 | 7.1 | 4.9 | |
| | | | | | | Found | 73.3 | 7.0 | 4.2 | |
| 16 | " | 2-Cl phenyl | " | " | " | Calc. | 75.6 | 7.1 | 4.9 | 56–58 |
| | | | | | | Found | 75.2 | 7.3 | 4.8 | |
| 17 | " | 4-Br phenyl | " | " | " | Calc. | 65.5 | 6.1 | 4.2 | 84–85 |
| | | | | | | Found | 65.1 | 6.3 | 4.0 | |
| 18 | phenyl | 2-(4-Cl phenyl)-thiazol-4-yl | 1 | H | H | Calc. | 68.4 | 5.7 | 7.6 | 98–100 |
| | | | | | | Found | 68.3 | 5.8 | 7.4 | |
| 19 | 4-$NO_2$ phenyl | 4-Cl phenyl | " | " | " | Calc. | 64.98 | 5.78 | 8.39 | 93–94 |
| | | | | | | Found | 65.23 | 5.77 | 8.47 | |
| 20 | phenyl | phenyl | " | phenyl | " | Calc. | 87.42 | 7.86 | 4.11 | 103–104 |
| | | | | | | Found | 87.87 | 7.79 | 4.15 | |
| 21 | 4-$NO_2$ phenyl | " | " | H | " | Calc. | 73.0 | 6.8 | 9.5 | |
| | | | | | | Found | 70.0 | 6.6 | 9.8 | |
| 22 | phenyl | 4-$^t$Bu phenyl | " | " | " | | | | | 95–96 |
| 23 | phenyl | 2,4-$Cl_2$ phenyl | 1 | H | H | Calc. | 67.39 | 5.93 | 4.45 | 59–60 |
| | | | | | | Found | 67.51 | 5.99 | 4.41 | |
| 24 | 4-$NO_2$ phenyl | $^nC_6H_{13}$ | 0 | — | — | Calc. | 70.3 | 9.0 | 9.7 | |
| | | | | | | Found | 67.1 | 8.7 | 9.5 | |
| 25 | phenyl | 4-biphenylyl | 1 | H | H | Calc. | 88.03 | 7.7 | 4.28 | 81–83 |
| | | | | | | Found | 87.58 | 7.61 | 4.34 | |
| 26 | 4-$NH_2$ phenyl | phenyl | " | " | " | Calc. | 81.16 | 8.32 | 10.52 | 81–82 |
| | | | | | | Found | 80.78 | 8.34 | 10.44 | |

TABLE I-continued

| # | R1 | R2 | n | R3 | R4 | | C | H | N | mp |
|---|---|---|---|---|---|---|---|---|---|---|
| 27 | phenyl | 4-CH₃O phenyl | " | " | " | Calc. | 81.1 | 8.24 | 4.98 | 56 |
| | | | | | | Found | 80.61 | 8.15 | 4.87 | |
| 28 | phenyl | 3-CF₃ phenyl | 1 | H | H | Calc. | 71.5 | 6.3 | 4.4 | |
| | | | | | | Found | 69.9 | 6.2 | 4.3 | |
| 29 (saccharin salt) | " | 4-Cl phenyl | " | " | " | Calc. | 64.0 | 5.4 | 6.0 | ≦75 deliquesces |
| | | | | | | Found | 62.8 | 5.5 | 5.7 | |
| 30 (oxalate) | " | " | " | " | " | Calc. | 70.2 | 6.4 | 4.2 | 230 decomp. |
| | | | | | | Found | 68.6 | 6.5 | 4.2 | |
| 31 (HCl salt) | " | " | " | " | " | Calc. | 67.1 | 6.6 | 4.3 | 256–258 |
| | | | | | | Found | 66.8 | 6.6 | 4.3 | |
| 32 | " | pyrid-2-yl | " | " | " | | | | | |
| 33 | phenyl | phenyl | 3 | H | H | Calc. | 86.0 | 9.0 | 5.0 | |
| | | | | | | Found | 85.4 | 9.0 | 5.3 | |
| 34 | " | naphth-1-yl | 1 | " | " | Calc. | 87.7 | 7.7 | 4.7 | 97–98 |
| | | | | | | Found | 87.3 | 7.8 | 4.6 | |
| 35 | 4-Br phenyl | 4-Cl phenyl | " | " | " | Calc. | 59.3 | 5.3 | 3.8 | 75–77 |
| | | | | | | Found | 58.2 | 5.3 | 3.9 | |
| 36 | " | ⁿC₄H₉ | 2 | " | " | Calc. | 62.96 | 8.08 | 4.32 | |
| | | | | | | Found | 63.21 | 8.14 | 4.51 | |
| 37 | phenyl | cyclohexyl | 1 | " | " | Calc. | 84.0 | 10.6 | 5.4 | 53–56 |
| | | | | | | Found | 83.4 | 10.6 | 6.5 | |
| 38 | 4-Cl phenyl | 4-Cl phenyl | 1 | H | H | Calc. | 67.5 | 5.98 | 4.37 | |
| | | | | | | Found | 66.52 | 5.98 | 4.29 | |
| 39 | phenyl | —CH₂CH₂CH=CH₂ | 2 | " | " | Calc. | 83.9 | 10.3 | 5.8 | |
| | | | | | | Found | 80.8 | 9.9 | 5.8 | |
| 40 | " | —CH₂CH≡CH | 3 | " | " | Calc. | 84.6 | 9.6 | 5.8 | |
| | | | | | | Found | 84.6 | 10.0 | 5.8 | |
| 41 | " | 4-CH₃ phenyl | 1 | " | " | Calc. | 85.6 | 8.7 | 5.3 | 60–62 |
| | | | | | | Found | 85.6 | 8.6 | 5.2 | |
| 42 | " | C₂H₅ | 3 | " | " | Calc. | 83.1 | 10.9 | 6.1 | |
| | | | | | | Found | 83.1 | 10.9 | 6.3 | |
| 43 | phenyl | C₇H₁₅ | 0 | — | — | Calc. | 83.3 | 11.3 | 5.4 | |
| | | | | | | Found | 79.2 | 10.8 | 5.0 | |
| 44 | " | phenyl | 1 | CH₃ | H | Calc. | 85.6 | 8.7 | 5.3 | |
| | | | | | | Found | 85.6 | 9.0 | 5.1 | |
| 45 | " | 2-CH₃ phenyl | " | H | H | Calc. | 85.99 | 8.73 | 5.28 | |
| | | | | | | Found | 84.57 | 8.57 | 5.38 | |
| 46 | " | 4-CF₃ phenyl | " | " | " | Calc. | 71.46 | 6.31 | 4.39 | 102–103 |
| | | | | | | Found | 71.26 | 6.52 | 4.4 | |
| 47 | " | 4-CN phenyl | " | " | " | Calc. | 82.57 | 7.29 | 10.14 | 117–118 |
| | | | | | | Found | 82.13 | 7.20 | 10.08 | |
| 48 | phenyl | naphth-2-yl | 1 | H | H | Calc. | 87.66 | 7.69 | 4.65 | 81–82 |
| | | | | | | Found | 87.6 | 7.7 | 4.74 | |
| 49 | " | 2,6-Cl₂ phenyl | " | " | " | Calc. | 67.51 | 5.98 | 4.37 | 107–108 |
| | | | | | | Found | 67.3 | 6.07 | 4.44 | |
| 50 | " | 4-CH₃OCO phenyl | " | " | " | Calc. | 77.64 | 7.49 | 4.53 | 89–90 |
| | | | | | | Found | 78.01 | 7.52 | 4.61 | |
| 51 | " | 3,4-Cl₂ phenyl | " | " | " | Calc. | 67.51 | 5.98 | 4.37 | 69–70 |
| | | | | | | Found | 67.88 | 5.77 | 4.41 | |
| 52 | " | 3-CH₃ phenyl | " | " | " | Calc. | 85.99 | 8.73 | 5.28 | |
| | | | | | | Found | 82.95 | 8.74 | 5.33 | |
| 53 | phenyl | —CH=CH—C₆H₅ | 1 | H | H | Calc. | 86.59 | 8.36 | 5.05 | |
| | | | | | | Found | 86.23 | 8.92 | 5.25 | |
| 54 | " | 2-OH cyclohexyl | 0 | — | — | Calc. | 78.7 | 9.7 | 5.4 | 121–123 |
| | | | | | | Found | 78.5 | 9.6 | 5.4 | |
| 55 | " | cyclohexyl | 0 | — | — | Calc. | 83.9 | 10.4 | 5.8 | 68–70 |
| | | | | | | Found | 84.0 | 10.2 | 6.0 | |
| 56 | 4-CH₃ phenyl | phenyl | 1 | H | H | Calc. | 85.99 | 8.74 | 5.28 | 45–47 |
| | | | | | | Found | 86.08 | 8.85 | 5.38 | |
| 57 | 2-CH₃ phenyl | " | " | " | " | Calc. | 85.99 | 8.74 | 5.28 | |
| | | | | | | Found | 85.85 | 8.78 | 5.56 | |
| 58 | 4-CH₃ phenyl | 4-Cl phenyl | 1 | H | H | Calc. | 76.11 | 7.4 | 4.67 | 68–70 |
| | | | | | | Found | 75.59 | 7.41 | 4.53 | |
| 59 | 3-CH₃ phenyl | phenyl | " | " | " | Calc. | 85.99 | 8.74 | 5.28 | |
| | | | | | | Found | 85.25 | 8.60 | 5.32 | |
| 60 | 4-CH₃ phenyl | ⁿC₅H₁₁ | " | " | " | Calc. | 83.33 | 11.27 | 5.4 | |
| | | | | | | Found | 82.36 | 11.60 | 4.79 | |
| 61 | 3-CH₃ phenyl | 4-Cl phenyl | " | " | " | Calc. | 76.11 | 7.4 | 4.67 | |
| | | | | | | Found | 75.67 | 7.35 | 4.48 | |
| 62 | phenyl | —CH₂CH(C₂H₅)—ⁿC₄H₉ | 0 | — | — | Calc. | 83.6 | 11.6 | 4.9 | |
| | | | | | | Found | 82.8 | 11.2 | 4.9 | |
| 63 | phenyl | —CH₂CH₂OC₆H₅ | 0 | — | — | Calc. | 81.1 | 8.2 | 5.0 | |
| | | | | | | Found | 79.5 | 7.9 | 4.7 | |
| 64 | 3-CH₃ phenyl | phenyl | 2 | H | H | Calc. | 86.0 | 9.0 | 5.0 | |

TABLE I-continued

| | | | | | | | | | | |
|---|---|---|---|---|---|---|---|---|---|---|
| 65 | " | nC3H7 | 3 | " | " | Found | 83.0 | 8.9 | 5.2 | |
| | | | | | | Calc. | 83.33 | 11.27 | 5.4 | |
| | | | | | | Found | 82.63 | 11.08 | 5.10 | |
| 66 | 4-CH3O phenyl | phenyl | 1 | " | " | Calc. | 81.1 | 8.24 | 4.98 | 71 |
| | | | | | | Found | 81.80 | 8.37 | 5.00 | |
| 67 | " | 4-Cl phenyl | " | " | " | Calc. | 72.25 | 7.02 | 4.43 | 91 |
| | | | | | | Found | 72.37 | 7.09 | 4.46 | |
| 68 | 4-CH3O phenyl | nC5H11 | 1 | H | H | Calc. | 78.49 | 10.61 | 5.09 | 43 |
| | | | | | | Found | 78.15 | 10.42 | 5.00 | |
| 69 | " | phenyl | 2 | " | " | Calc. | 81.31 | 8.53 | 4.74 | 63 |
| | | | | | | Found | 81.01 | 8.46 | 4.78 | |
| 70 | " | 4-Cl phenyl | " | " | " | Calc. | 72.82 | 7.33 | 4.25 | 89 |
| | | | | | | Found | 73.21 | 7.47 | 4.36 | |
| 71 | 4-biphenyl | 4-Cl phenyl | 1 | " | " | Calc. | 79.65 | 6.68 | 3.87 | |
| | | | | | | Found | 80.15 | 6.70 | 3.55 | |
| 72 | " | nC4H9 | 2 | " | " | Calc. | 85.9 | 9.7 | 4.4 | 69–70 |
| | | | | | | Found | 85.7 | 9.9 | 5.0 | |
| 73 | 4-biphenyl | phenyl | 2 | H | H | Calc. | 87.3 | 8.0 | 4.1 | 122–124 |
| | | | | | | Found | 88.1 | 7.9 | 4.2 | |
| 74 | naphth-1-yl | " | 1 | " | " | Calc. | 87.7 | 7.7 | 4.7 | 86–88 |
| | | | | | | Found | 87.1 | 7.7 | 4.5 | |
| 75 | " | 4-Cl phenyl | " | " | " | Calc. | 78.7 | 6.6 | 4.2 | 94 |
| | | | | | | Found | 78.2 | 6.7 | 4.0 | |
| 76 | " | nC3H7 | 3 | " | " | Calc. | 85.4 | 9.9 | 4.7 | |
| | | | | | | Found | 84.8 | 9.8 | 4.4 | |
| 77 | naphth-2-yl | phenyl | 1 | " | " | Calc. | 87.7 | 7.7 | 4.7 | 101–103 |
| | | | | | | Found | 87.5 | 7.6 | 4.5 | |
| 78 (acetate) | phenyl | 4-Cl phenyl | 1 | H | H | Calc. | 68.5 | 7.0 | 4.1 | 50–52 |
| | | | | | | Found | 67.7 | 7.0 | 3.8 | |
| 79 (lactate) | " | " | " | " | " | Calc. | 67.1 | 7.0 | 3.7 | 112–119 |
| | | | | | | Found | 66.4 | 7.0 | 3.6 | |
| 80 (mandelate) | " | " | " | " | " | Calc. | 71.3 | 6.4 | 3.2 | 136–139 |
| | | | | | | Found | 71.5 | 6.4 | 2.9 | |
| 81 (benzoate) | " | " | " | " | " | Calc. | 73.6 | 6.4 | 3.4 | 58–65 |
| | | | | | | Found | 73.0 | 6.4 | 3.3 | |
| 82 (laurate) | " | " | " | " | " | Calc. | 74.1 | 9.1 | 2.9 | |
| | | | | | | Found | 73.8 | 9.4 | 2.5 | |
| 83 (phosphonate) | phenyl | 4-Cl phenyl | 1 | H | H | Calc. | 66.1 | 6.6 | 4.3 | 148–154 |
| | | | | | | Found | 66.3 | 6.7 | 4.3 | |
| 84 (dodecyl-benzene-sulphonate) | " | " | " | " | " | Calc. | 70.6 | 8.2 | 2.3 | 125–128 |
| | | | | | | Found | 70.3 | 8.2 | 2.1 | |
| 85 | naphth-2-yl | " | " | " | " | Calc. | 78.7 | 6.6 | 4.2 | 116–118 |
| | | | | | | Found | 78.2 | 6.4 | 3.6 | |
| 86 | " | nC6H13 | 0 | — | — | Calc. | 85.4 | 9.9 | 4.7 | 45 |
| | | | | | | Found | 85.4 | 9.9 | 4.6 | |
| 87 | " | phenyl | 2 | H | H | Calc. | 87.6 | 8.0 | 4.4 | 78 |
| | | | | | | Found | 87.6 | 8.2 | 4.2 | |

EXAMPLE 88

The fungicidal activity of compounds of the invention was investigated by means of the following tests.

(a) Antisporulant activity against vine downy mildew (*plasmopara viticola*; PVA)

The test is a direct antisporulant one using a foliar spray. The lower surfaces of leaves of whole vine plants (cv Cabernst Sauvignon) are inoculated by spraying with an aqueous suspension containing $2.5 \times 10^4$ zoosporangia/ml 2 days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). Plants are treated using an automated sprayline with an atomising nozzle. The concentration of the compound is 1000 ppm, and the spray volume is 700 l/ha. After spraying, the plants are returned to normal glasshouse conditions for 96 hours and are then transferred to the high humidity compartment for 24 hours to induce sporulation, prior to assessment. Assessment is based on the percentage of the leaf area covered by spotclarion compared with that on control leaves.

(b) Direct protectant activity against vine downy mildew (Plasmopara viticola; PVP)

The test is a direct protectant one using a foliar spray. The lower surfaces of leaves of whole vine plants (cv Cabernst Sauvignon) are sprayed with the test compound at a dosage of 1000 ppm using an automated sprayline as described under (a), and after a subsequent period of 24 hours under normal glasshouse conditions the lower surfaces of the leaves are inoculated by spraying with an aqueous solution containing 2.5×104 zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(c) Direct protectant activity against broad bean grey mould (*Botrytis cinerea*; BCB)

The test is a direct protectant one using a foliar spray. The upper surfaces of leaves of broad bean plants (cv The Sutton) are sprayed with the test compound at a dosage of 1000 ppm using an automated sprayline as described under (a). 24 hours after spraying the leaves are inoculated with an aqueous suspension containing $10^5$ conidia/ml. For 4 days after inoculation plants are kept moist in a humidity compartment at 21° C. Disease is assessed 4 days after inoculation, based on the percentage of leaf surface area covered by lesions.

(d) Activity against wheat leafspot (*Leptosphaeria nodorum*; LN.)

The test is a direct therapeutic one, using a foliar spray. Leaves of wheat plants (cv Norman), at the single leaf stage, are inoculated by spraying with an aqueous suspension containing $1\times10^6$ spores/mi. The inoculated plants are kept for 24 hours in a high humidity compartment prior to treatment. The plants are sprayed with a solution of the test compound at a dosage of 1000 ppm using an automated sprayline as described under (a). After drying, the plants are kept for 6–8 days at 22° C. and moderate humidity, followed by assessment. Assessment is based on the density of lesions per leaf compared with that on leaves of control plants.

(e) Activity against barley powdery mildew (*Erysiphe qramini* f.sp. hordei; EG)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1000 ppm using an automated sprayline as described under (a). After drying, plants are returned to a compartment at 20°–25° C. and moderate humidity for up to 7 days, followed by assessment. Assessment is based on the percentage of leaf area covered by sporulation compared with that on leaves of control plants.

(f) Activity against wheat brown rust (*Puccinia recondita*; PR)

The test is a direct protectant one using a foliar spray. Wheat seedlings (cv Avalon) are grown to the 1–1% leaf stage. The plants are then sprayed with the test compound at a dosage of 1000 ppm using an automated sprayline as described under (a). Test compounds are applied as solutions or suspensions in a mixture of acetone and water (50:50 v/v) containing 0.04% surfactant ("MEN 20"—Trade Mark). 18–24 hours after treatment, the seedlings are inoculated by spraying the plants from all sides with an aqueous spore suspension containing about $10^5$ spores/m1. For 18 hours after inoculation, the plants are kept in high humidity conditions at a temperature of 20°–22° C. Thereafter, the plants are kept in ambient glasshouse conditions, that is, in moderate relative humidity and at a temperature of 20° C. The disease is assessed 10 days after inoculation on the basis of the percentage of the plant covered by sporulating pustules compared with that on the control plants.

(g) Activity against rice leaf blast (*Pyricularia oryzae*; PO)

The test is a direct therapeutic one using a foliar spray. The leaves of rice seedlings (cv Aichiaishi—about 30 seedlings per pot) are sprayed with an aqueous suspension containing $10^5$ spores/ml 20–24 hours prior to treatment with the test compound. The inoculated plants are kept overnight in high humidity and then allowed to dry before spraying with the test compound at a dosage of 1000 ppm using an automated sprayline as described under (a). After treatment the plants are kept in a rice compartment at 25°–30° C. and high humidity. Assessments are made 4–5 days after treatment and are based on the density of necrotic lesions per leaf when compared with control plants.

(h) Activity against tomato early blight (*Alternaria solani*; AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20"—Trade Mark). One day after treatment the seedlings are inoculated by spraying the leaf upper surfaces with a suspension of *A. solani* conidia containing $10^4$ spores/mi. For 4 days after inoculation plants are kept moist in a humidity compartment at 21° C. Disease is assessed 4 days after inoculation, based on the percentage of leaf surface area covered by lesions.

(i) Activity against wheat eyespot in-vitro (*Pseudocercosporella herpotrichoides*; PHI)

This test measures the in vitro activity of compounds against the fungus causing wheat eyespot. The test compound is dissolved or suspended in acetone and is added to molten half strength Potato Dextrose Agar to give a final concentration of 100 ppm compound and 3.5% acetone. After agar has set, plates are inoculated with 6mm diameter plugs of agar/mycelium taken from a 14 day old culture of *P. herpotrichoides*. Plates are incubated at 20° C. for 12 days and radial growth from the inoculation plug is measured.

(j) Activity against Fusarium in-vitro (*Fusarium culmorum*; FSI)

This test measures the in vitro activity of compounds against a species of Fusarium that causes stem and root rots. The test compound is dissolved or suspended in acetone and added to molten half strength Potato Dextrose Agar to give a final concentration of 100ppm compound and 3.5% acetone. After agar has set, plates are inoculated with 6mm diameter plugs of agar and mycelium taken from a 7 day old culture of Fusarium sp.. Plates are incubated at 20° C. for 5 days and radial growth from the plug is measured.

The extent of disease control in all the above tests is expressed as a rating compared with either an untreated control or a diluent-sprayed-control, according to the criteria:

0=less than 50% disease control
1=about 50–80% disease control
2=greater than 80% disease control The results of these tests are set out in Table II below:

TABLE II

| Compound Ex. No. | PVA | PVP | BCB | LN | EG | PR | PO | AS | PHI | FSI |
|---|---|---|---|---|---|---|---|---|---|---|
| 1 |  | 1 |  |  | 2 |  |  |  | 2 |  |
| 2 |  | 1 |  |  | 2 |  |  |  |  |  |
| 3 |  |  |  |  | 2 |  |  |  | 2 |  |
| 4 |  |  |  | 1 | 2 |  |  |  | 2 |  |
| 5 |  | 1 |  |  | 2 |  |  |  | 2 |  |
| 6 | 1 |  |  |  | 2 |  |  | 1 | 2 |  |
| 7 |  |  |  |  | 2 |  |  |  | 2 |  |
| 8 |  |  |  |  |  | 1 |  |  | 2 |  |
| 9 |  |  |  | 2 | 2 |  |  |  | 1 |  |
| 10 |  | 2 |  | 2 | 1 |  |  |  |  |  |
| 11 |  |  |  |  | 2 |  |  |  | 2 |  |
| 12 |  |  |  | 2 | 2 |  |  |  | 1 |  |
| 13 | 1 |  |  |  | 2 |  |  |  | 1 |  |
| 14 |  |  |  |  | 2 |  |  | 1 | 1 | 1 |
| 15 |  |  |  |  | 2 |  |  |  | 1 |  |
| 16 |  | 2 |  |  | 1 |  |  |  |  |  |
| 17 |  | 1 | 1 | 2 |  |  |  | 2 |  |  |
| 18 |  | 2 | 1 |  | 1 |  |  |  | 1 |  |
| 19 |  | 1 |  | 1 | 1 |  |  |  | 1 |  |
| 20 |  | 1 |  |  | 1 |  |  |  | 1 |  |
| 21 |  |  | 1 |  |  |  |  | 2 |  |  |
| 22 |  |  |  |  | 2 |  |  |  | 1 |  |
| 23 |  |  |  |  | 2 |  |  |  | 1 |  |
| 23 |  |  |  |  | 2 |  |  |  | 2 |  |
| 24 |  |  |  |  | 2 |  |  |  | 1 |  |
| 25 |  | 1 |  |  | 2 | 1 |  |  |  | 1 |
| 26 |  | 2 | 1 | 1 |  |  |  |  |  |  |
| 27 |  | 1 |  |  | 2 |  |  |  | 1 |  |
| 28 |  |  |  |  | 2 |  |  |  |  |  |
| 29 |  | 1 |  | 1 | 2 |  |  |  | 1 |  |
| 30 |  | 1 |  |  | 2 |  |  | 1 |  |  |
| 31 |  | 2 |  |  | 2 |  |  |  |  |  |
| 32 |  |  | 1 |  | 1 |  |  |  |  |  |
| 33 |  |  |  |  | 2 |  |  |  | 1 |  |
| 34 |  |  |  |  | 2 |  |  |  |  |  |
| 35 |  | 1 |  | 1 | 2 |  |  |  |  |  |
| 36 |  |  |  | 2 | 2 |  |  |  | 1 |  |
| 37 |  |  |  |  | 2 |  |  |  | 1 |  |
| 38 | 1 | 1 |  | 2 | 2 | 1 |  |  | 1 |  |
| 39 |  |  | 2 |  | 2 |  |  |  | 1 |  |
| 40 |  |  | 2 |  | 2 |  |  |  |  |  |
| 41 |  |  | 2 |  | 2 | 1 |  |  | 1 |  |
| 42 |  |  | 2 |  | 2 |  |  |  | 1 |  |
| 43 |  |  |  | 2 | 2 |  |  |  | 1 |  |
| 44 |  |  |  |  | 2 | 1 |  |  | 1 |  |
| 45 |  |  |  | 1 | 2 | 1 |  |  |  |  |
| 46 |  |  |  | 1 | 2 | 1 |  |  |  |  |
| 47 |  |  |  |  | 2 |  |  | 1 |  |  |
| 48 |  |  |  |  | 2 | 1 |  |  |  |  |
| 49 |  |  |  |  |  | 1 |  |  |  |  |
| 50 |  |  |  |  | 2 | 1 | 1 |  |  |  |
| 51 |  |  |  |  | 2 | 1 |  |  |  |  |
| 52 |  |  |  |  | 2 | 1 |  |  |  |  |
| 53 |  |  |  |  | 2 | 1 |  |  |  |  |
| 54 |  |  |  |  |  |  |  | 1 |  |  |
| 55 |  |  |  | 1 | 1 |  |  |  | 1 |  |
| 56 |  |  |  |  | 2 |  |  |  | 1 |  |
| 57 |  |  |  | 1 |  |  |  |  | 1 |  |
| 58 |  |  |  |  | 2 |  |  |  | 1 |  |
| 59 |  |  |  |  | 2 |  |  |  | 1 |  |
| 60 |  |  |  | 1 | 2 |  |  |  | 1 |  |
| 61 |  |  |  |  |  |  |  |  | 1 |  |
| 62 |  |  |  |  | 2 |  |  |  | 1 |  |
| 63 |  |  |  |  | 2 |  |  |  | 1 |  |
| 64 |  |  |  | 1 | 1 |  | 1 |  | 1 |  |
| 65 |  |  |  | 1 | 2 |  |  |  | 1 |  |
| 66 |  |  |  |  | 2 |  |  |  | 1 |  |
| 67 |  |  |  | 1 | 2 |  |  |  | 1 |  |
| 68 |  |  |  |  | 2 |  |  |  | 1 |  |
| 69 |  |  |  | 1 | 2 |  |  |  | 1 |  |
| 70 |  |  |  | 1 | 2 |  |  |  | 1 |  |
| 71 |  |  |  |  | 2 | 1 |  |  |  |  |
| 72 |  |  |  |  | 2 |  |  |  | 2 |  |
| 73 |  |  | 1 |  | 2 |  |  |  | 2 |  |
| 74 |  |  |  |  |  |  |  |  | 1 |  |
| 75 |  |  |  |  |  |  |  |  | 1 |  |

TABLE II-continued

| Compound Ex. No. | PVA | PVP | BCB | LN | EG | PR | PO | AS | PHI | FSI |
|---|---|---|---|---|---|---|---|---|---|---|
| 76 | | | | 1 | 2 | | | | | |
| 77 | | | | 1 | 2 | | | | 2 | 1 |
| 78 | | | | | 2 | | | | 2 | 1 |
| 79 | | | | 1 | 2 | | | | 2 | |
| 80 | | | | | 2 | | | | 2 | |
| 81 | | 2 | | | 2 | | | | 2 | |
| 82 | | | | | 2 | | | | 1 | |
| 83 | | | 2 | | 2 | | | | 1 | |
| 84 | | | 2 | | 2 | | 1 | | 1 | |
| 85 | | | | | 2 | | 1 | | 1 | 1 |
| 86 | | | | | 2 | | | | 2 | 2 |
| 87 | | 2 | | | 2 | | | | 2 | 1 |

We claim:

1. A compound of the formula:

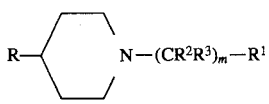

or an acid-addition salt thereof, in which

R represents phenyl;

$R^1$ represents $C_{1-12}$ alkyl, $C_{2-12}$ alkenyl, $C_{2-12}$ alkynyl, $C_{3-8}$ cycloalkyl, naphthyl, phenyl, pyridyl or thiazolyl group, each group optionally substituted by one or more substituents selected from halogen atoms, nitro, cyano, hydroxyl, $C_{1-4}$ alkyl, $C_{1-4}$ haloalkyl, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, halophenyl, and phenoxy groups;

m is 1; and each of $R^2$ and $R^3$ is independently selected from a group consisting of hydrogen atoms, $C_{1-4}$ alkyl and phenyl groups.

2. A compound according to claim 1, wherein each $R^2$ and $R^3$ is hydrogen.

3. A compound according to claim 1, wherein $R^1$ is phenyl substituted by at least one halogen atom.

4. A fungicidal composition which comprises a carrier and, as active ingredient, a compound of the formula:

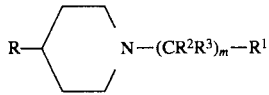

or an acid-addition salt thereof, in which

R represents phenyl;

$R^1$ represents $C_{1-12}$ alkyl, $C_{2-12}$ alkenyl, $C_{2-12}$ alkynyl, $C_{3-8}$ cycloalkyl, naphthyl, phenyl, pyridyl or thiazolyl group, each group optionally substituted by one or more substituents selected from halogen atoms, nitro, cyano, hydroxyl, $C_{1-4}$ alkyl, $C_{1-4}$ haloalkyl, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, halophenyl, and phenoxy groups;

m is 1; and each of $R^2$ and $R^3$ is independently selected from a group consisting of hydrogen atoms, $C_{1-4}$ alkyl and phenyl groups.

5. A composition according to claim 4, wherein each $R^2$ and $R^3$ is hydrogen.

6. A composition according to claim 4, wherein $R^1$ is phenyl substituted by at least one halogen atom.

7. A composition according to claim 4, which comprises at least two carriers, at least one of which is a surface active agent.

8. A method of combating fungus at a locus, which comprises treating the locus with an effective amount of a compound of the formula:

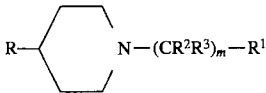

or an acid-addition salt thereof, in which

R represents phenyl;

$R^1$ represents $C_{1-12}$ alkyl, $C_{2-12}$ alkenyl, $C_{2-12}$ alkynyl, $C_{3-8}$ cycloalkyl, naphthyl, phenyl, pyridyl or thiazolyl group, each group optionally substituted by one or more substituents selected from halogen atoms, nitro, cyano, hydroxyl, $C_{1-4}$ alkyl, $C_{1-4}$ haloalkyl, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, halophenyl, and phenoxy groups;

m is 1; and each of $R^2$ and $R^3$ is independently selected from a group consisting of hydrogen atoms, $C_{1-4}$ alkyl and phenyl groups.

9. A method according to claim 8, wherein each $R^2$ and $R^3$ is hydrogen.

10. A method according to claim 8, wherein $R^1$ is phenyl substituted by at least one halogen atom.

11. A compound of the formula:

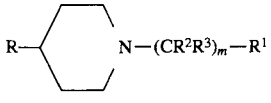

or an acid-addition salt thereof, in which

R is phenyl;

$R^1$ is phenyl substituted by one or more halogen atoms;

each $R^2$ and $R^3$ is independently selected from hydrogen and $C_{1-4}$ alkyl; and m is 1.

12. A compound according to claim 11, wherein $R^1$ is phenyl substituted by one or more chlorine atoms.

13. A compound according to claim 11, wherein $R^1$ is 4-chlorophenyl.

14. A compound according to claim 11, wherein $R^2$ and $R^3$ are each hydrogen.

15. A compound according to claim 13, wherein $R^2$ and $R^3$ are each hydrogen.

16. A fungicidal composition which comprises a carrier and, as active ingredient, a compound of the formula:

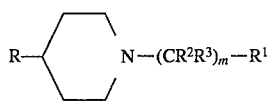 (I)

or an acid-addition salt thereof, in which

R is phenyl;

R¹ is phenyl substituted by one or more halogen atoms;

each R² and R³ is independently selected from hydrogen and $C_{1-4}$ alkyl; and m is 1.

17. A composition according to claim 16, wherein R¹ is phenyl substituted by one or more chlorine atoms.

18. A composition according to claim 16, wherein R¹ is 4-chloro phenyl.

19. A composition according to claim 16, wherein R² and R³ are each hydrogen.

20. A composition according to claim 18, wherein R² and R³ are each hydrogen.

21. A method of combating fungus at a locus, which comprises treating the locus with an effective amount of a compound of the formula:

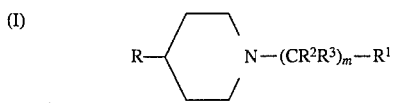 (I)

or an acid-addition salt thereof, in which

R represents phenyl;

R¹ is phenyl substituted by one or more halogen atoms;

each R² and R³ is independently selected from hydrogen and $C_{1-4}$ alkyl; and m is 1.

22. A method according to claim 21, wherein R¹ is phenyl substituted by one or more chlorine atoms.

23. A method according to claim 21, wherein R¹ is 4-chloro phenyl.

24. A method according to claim 21, wherein R² and R³ are each hydrogen.

25. A method according to claim 23, wherein R² and R³ are each hydrogen.

* * * * *